United States Patent [19]

Dahlquist

[11] Patent Number: 4,769,544
[45] Date of Patent: Sep. 6, 1988

[54] SYSTEM AND PROCESS FOR MEASURING FIBERGLASS

[75] Inventor: John A. Dahlquist, Palo Alto, Calif.

[73] Assignee: Measurex Corporation, Cupertino, Calif.

[21] Appl. No.: 616,352

[22] Filed: Jun. 1, 1984

[51] Int. Cl.⁴ .................. G01J 1/00; G01N 21/75
[52] U.S. Cl. .................. 250/339; 250/341; 436/34
[58] Field of Search ........... 250/339, 341; 436/34, 436/85, 164

[56] References Cited

U.S. PATENT DOCUMENTS

| | | | |
|---|---|---|---|
| 3,793,524 | 2/1974 | Howarth | 250/339 |
| 4,097,743 | 6/1978 | Carlson | 250/339 |
| 4,363,968 | 12/1982 | McGowan et al. | 250/339 |
| 4,609,628 | 9/1986 | Aschenbeck | 436/34 |

FOREIGN PATENT DOCUMENTS 2368038 10/1976 France.
WO84/01430 4/1984 PCT Int'l Appl..
2044443 8/1979 United Kingdom.

OTHER PUBLICATIONS

Measurex, "Infrand®V Moisture Sensor 2258,2259,2260", 1983.
Measurex 2001, "Infrared Thickness Sensor 2335", 1977.
599 Le Nouvel Automatisme, vol. 28 (1983) Oct. No. 41, Paris France.
2417 Optical Engineering, vol. 22 (1983) Jul./Aug., No. 4, Bellingham, Washington, USA.

Primary Examiner—Janice A. Howell
Attorney, Agent, or Firm—Spensley Horn Jubas & Lubitz

[57] ABSTRACT

The present invention is a device to measure the degree of cure of fiberglass using only infrared radiation. Particular frequencies of infrared radiation are used to determine the value of a cure-sensitive function and also the value of as cure-insensitive function and from a combination of the values of the functions, a property of fiberglass is determined.

9 Claims, 3 Drawing Sheets

4,769,544

SYSTEM AND PROCESS FOR MEASURING FIBERGLASS

BACKGROUND OF THE INVENTION

1. The Field of the Invention

This application concerns a system and a process for measuring the degree of cure of fiberglass.

2. State of the Art

Fiberglass contains glass fibers and binder which includes water and resin. The purpose of the binder is to hold the glass fibers together. In some cases the term fiberglass can be used to mean only the glass fibers; however, as used herein the term fiberglass means the mixture of glass fibers and binder.

During the manufacture of fiberglass, binder is mixed with glass fibers and the mixture is cured by heating. During the curing process the binder becomes relatively solid and cohesive and is instrumental in bonding the glass fibers to each other. During the manufacturing process it is important to know the degree to which the fiberglass is cured so that the minimum amount of heat energy can be applied to the fiberglass while insuring that sufficient heat energy is provided to result in adequate bonding of the glass fibers.

U.S. Pat. No. 4,363,968, the inventors of which are McGowan et al., teaches a system for measuring the degree of cure of fiberglass. The device taught in the patent uses infrared radiation and x-ray or gamma ray radiation to measure the degree of cure of fiberglass. In building and operating a device to measure the degree of cure, one must utilize the proper wavelength of infrared radiation in order to obtain correct results. However, the patent fails to teach the proper wavelength of infrared radiation which should be used to measure the degree of cure.

A further shortcoming of the McGowan patent is that x-rays or gamma rays must be used in conjunction with infrared radiation in order to determine the degree of cure. An x-ray or gamma ray source is different from an infrared radiation source and therefore the device utilizes two sources of radiation which is a more complicated and error prone system than a single source of radiation.

OBJECTS OF THE INVENTION

An object of the present invention is a device to measure the degree of cure of fiberglass using only infrared radiation and not x-ray or gamma ray radiation.

Another object of the present invention is a process utilizing particular frequencies of infrared radiation to determine the degree of cure.

Further objects and advantages of the present invention can be ascertained by reference to the specification and drawings, which are offered by way of example and not in limitation of invention which is defined by the claims and equivalents.

DETAILED DESCRIPTION OF THE PREFERRED EMBODIMENTS

Figure 1:
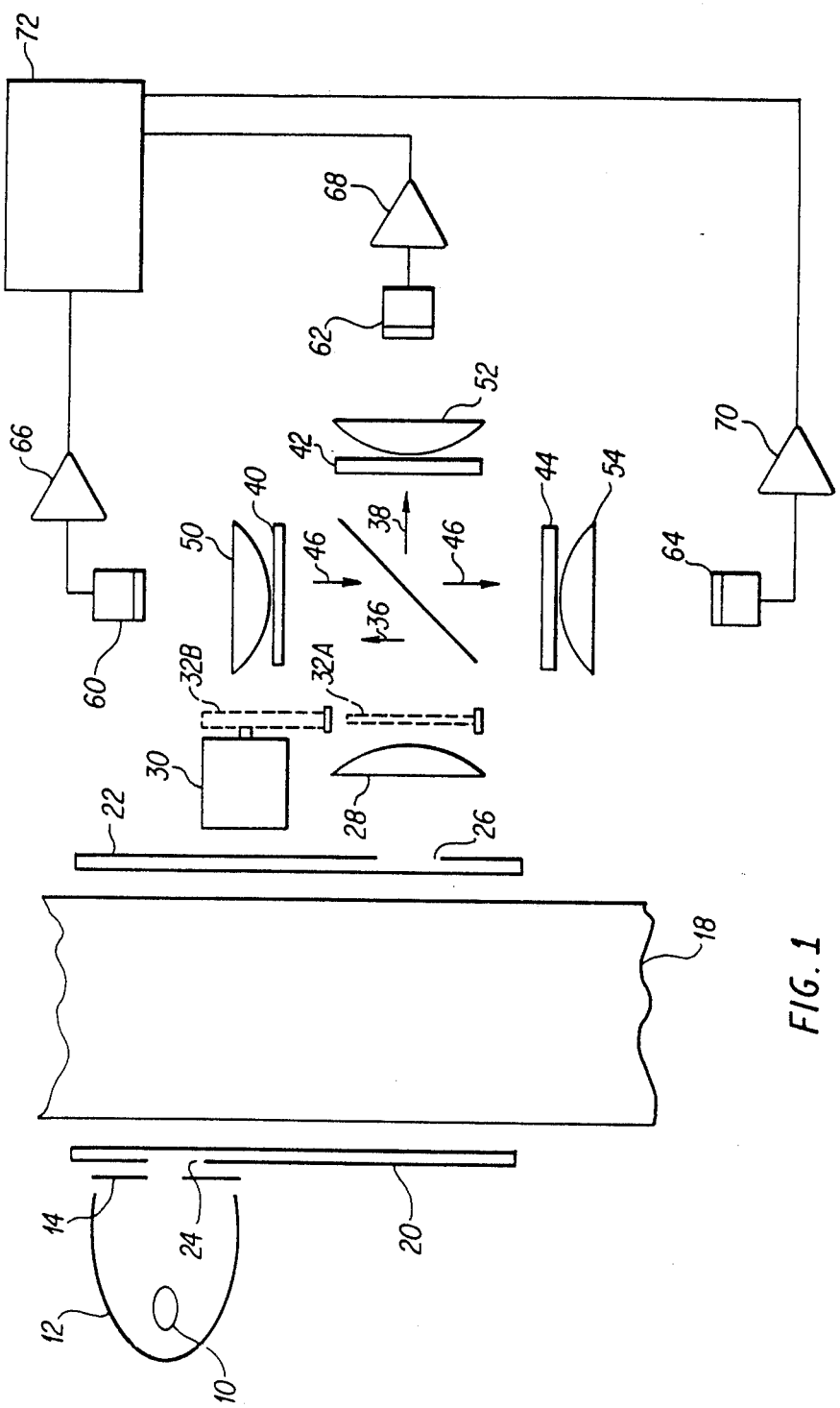
FIG. 1 is a schematic illustration of one embodiment.

The embodiment shown in FIG. 1 includes a source 10 of infrared radiation which is mounted in an elliptical reflector 12. The source 10 generates a spectrum of infrared radiation which includes the wavelengths which are used in the measurements performed herein. In the present embodiment the wavelengths of about 1.5 microns, 1.6 microns and 1.7 microns are used for measurement purposes. Thus the source 10 generates a spectrum including those three wavelengths and wavelengths in between as well as some wavelengths below 1.5 microns and above 1.7 microns. A light chopper 14 is located adjacent the elliptical reflector to chop the light emanating from the sources; that is, the chopper 14 interrupts the beam of radiation at a predetermined frequency.

The mat of fiberglass 18 is located near the reflector 12 so that light passing through the chopper 14 impinges upon the mat 18. In practice, the mat 18 normally is moving relative to the source 10 and the other elements of the present system so that the system scans across the mat to measure the mat at various points.

Two diffusing reflector plates 20 and 22 are mounted to either side of the mat 18 are stationary with respect to the reflector 12. The plates 20 and 22 include reflecting material to reflect radiation traveling away from the mat 18, and the plates 20 and 22 also include diffusing material so that the reflected light is also diffused. The first reflecting plate 20 includes a non-reflecting portion 24 formed in the reflecting material in alignment with the opening in the light chopper 14, and the second plate 22 includes a similar portion 26 located out of alignment with the portion 24 and light chopper 14. Thus, radiation emanating from the source 10 passes through the chopper 14 and the portion 24 and impinges upon the mat 18. Some of the radiation passes through the mat 18 and some is reflected, and the radiation is repeatedly transmitted through and reflected from the mat while being diffused and reflected between plates 20 and 22. Some of the radiation leaves the plates through the non-reflecting portion 26. The plates 20 and 22 will not be described in detail herein since they are substantially the same as the diffusing sheets and reflecting layers taught in U.S. Pat. No. 3,793,524.

The radiation which leaves the second plate 22 via portion 26 impinges upon lens 28. The radiation leaving lens 28 and moving toward the right can be attenuated by a positionable neutral density flag 32 which can be moved by solenoid 30 to either position 32a to attenuate the radiation or position 32b which allows the radiation to pass toward the right. A beam splitter 34 is located to the right of the lens 28 so that radiation impacting upon the beam splitter 34 is partially reflected upward and partially allowed to pass to the right as illustrated by the arrows 36 and 38, respectively.

First, second, and third filters 40, 42 and 44, respectively, are positioned around the beam splitter 34. The first filter is located to receive radiation 36, and the second filter 42 is located to receive radiation 38. The first filter 40 transmits radiation having a wavelength of about 1.6 microns, and reflects substantially all other radiation. The second filter 42 transmits radiation of about 1.7 microns and reflects substantially all other radiation, and the third filter 44 transmits radiation of about 1.5 microns and reflects substantially all other radiation. Thus, radiation having a wavelength of about 1.5 microns is reflected from the first filter 40 as indicated by arrow 46, and part of the radiation 46 passes through the beam splitter 34 to impinge upon the third filter 44 and be transmitted therethrough.

Lenses 50, 52 and 54 are located adjacent the three respective filters to focus the radiation passing through each filter onto a respective detectors 60, 62 and 64. The three detectors 60, 62 and 64 each measure the intensity of the radiation impinging thereon and generate an electrical signal proportional to the radiation. The detectors are each electrically coupled to an amplifier 66, 68 and 70 respectively. The amplifiers 66, 68 and 70 are each connected to support electronics and computer 72 for processing the information received from the amplifiers.

In operation, infrared radiation is generated by the source 10 and is thereafter diffused and reflected through the mat of fiberglass 18. After leaving the mat 18 the light impinges upon the beam splitter 34, and the 1.6 micron part of the beam is detected at detector 60, the 1.7 micron portion of the beam is detected by detector 62, and the 1.5 micron segment of the beam is detected by detector 64. The support electronics and computer 72 perform certain calculations upon the information received from the amplifiers. Specifically, the support electronics and computer 72 accomplish the following calculations:

$$R - 1 = a \times B \left[ 1 + b \left( \frac{C}{C_0} - 1 \right) \right] \quad (1)$$

$$R' - 1 = a' \times B \left[ 1 - b' \left( \frac{C}{C_0} - 1 \right) \right] \quad (2)$$

R is the so-called gauge ratio at the 1.6 and 1.7 micron wavelengths. In other words, R is the intensity of the signal received by detector 60 divided by the intensity of the signal received by detector 62. Likewise, R' is a gauge ratio at the 1.6 and 1.5 micron wavelengths. In other words, R' is the intensity of the signal received by the detector 60 divided by the intensity of signal received by detector 64.

With respect to the above equations, a, a', b and b' are constants. B represents the amount of binder in the fiberglass, C represents the degree of cure, and $C_0$, represents the degree of nominal cure. The degree of nominal cure, $C_0$, is a reference degree of cure or a target cure. Thus ($C/C_0$) is the relative degree of cure with respect to the target or nominal cure. From equations (1) and (2) it can be seen that R increases as ($C/C_0$) increases and that R' decreases as ($C/C_0$) increases. The reason for this is that the 1.7 micron wavelength is attenuated more by cured fiberglass than by less-cured fiberglass, whereas the 1.5 micron wavelength is attenuated less by cured fiberglass than by less-cured fiberglass. In other words, the attenuation of the 1.7 and 1.5 micron wavelengths varies with varying degree of cure, the variations being different for the 1.7 and 1.5 micron attenuation. That is, the 1.7 micron wavelength is attenuated as a function of the degree of cure, and the 1.5 micron wavelength is attenuated as a different function of the degree of cure. The 1.6 micron wavelength is substantially unaffected by the degree of cure of the binder or by the amount of binder. However, the 1.6 micron wavelength is affected by losses and attenuation due to scattering by the glass fibers. The 1.7 and 1.5 micron radiation are also affected by scattering. Thus the ratios R and R' are used to permit determination of the degree of cure unaffected by the quantity of glass fibers in the fiberglass. These three wavelengths were determined experimentally.

In practice equations (1) and (2) are solved so that:

$$B = A_1 R + A_2 R' + A_3 \quad (3)$$

$$\frac{C}{C_0} = A_4 \left[ \frac{R - 1}{R' - 1} \right] \quad (4)$$

where $A_1$, $A_2$, $A_3$ and $A_4$ are calibration constants. In other words, $B = f_1(R) + f_2(R')$ and $(C/C_0) = f_3(R, R')$.

Alternatively, equations (1) and (2) could be solved using standard techniques for solving two equations in two unknowns to determine B and ($C/C_0$). Before utilizing this system to measure the cure of an actual mat of fiberglass, the system is operated in a laboratory environment to determine the calibration constants $A_1$, $A_2$, $A_3$ and $A_4$ using samples of fiberglass having known parameters, or, alternatively, a "trial run" is made in the factory.

The purpose of the solenoid 30 is to move the flag 32 from position 32b, which is the normal operating position, to position 32a which is a standardization position. When the flag 32 is in the position 32a, the radiation is attenuated by passage through the neutral density flag so that the amount of radiation reaching the filters 40, 42 and 44 and detectors 60, 62 and 64 does not cause saturation. Subsequent on-line measurements are normalized by the signals obtained during standardization.

Figure 2:
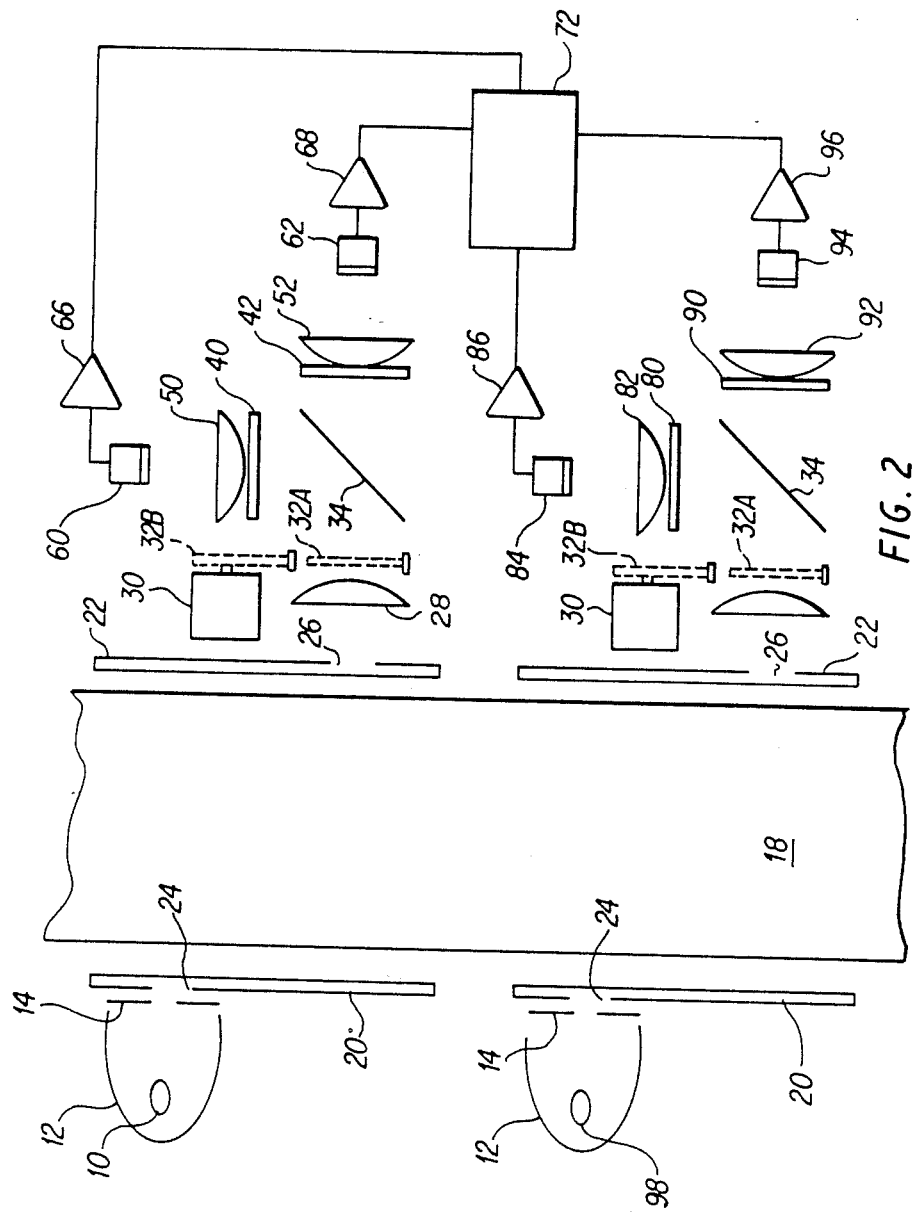
FIG. 2 is a schematic illustration of another embodiment.

FIG. 2 illustrates a second embodiment of the present invention. According to the FIG. 2 embodiment the parts of the system bearing the same numbers as those shown in the FIG. 1 system are the same. The FIG. 2 system has four systems of filters, lenses, detectors and amplifiers rather than three sets as in the FIG. 1 system. The FIG. 2 system includes first filler 40 and second filter 42 which transmit 1.6 micron and 1.7 micron radiation, respectively as in the FIG. 1 embodiment. The system also includes a third filter 80 which transmits radiation having a wavelength of substantially 2.30 microns, and a fourth filter 90 transmits radiation substantially having a wavelength of 2.35 microns. The system also includes a detection and amplification system co-acting with the third filter 80, which includes lens 82, detector 84 and amplifier 86. The fourth filter 90 is operated in connection with lens 92, detector 94 and amplifier 96. All four amplifiers 66, 68, 86 and 96 are coupled to the electronics and computer 72. The light source 98 produces a beam of radiation including at least 2.30 and 2.35 microns wavelengths.

In operation of the FIG. 2 embodiment, the computer 72 utilizes the following equations to determine the degree of cure.

$$R - 1 = a \times B \left[ 1 + b \left( \frac{C}{C_0} - 1 \right) \right] \quad (5)$$

$$R'' - 1 = a'' \times B \quad (6)$$

In equation (5) all the parameters are the same as discussed above with respect to equation (1). In equation (6) R'' is the gauge ratio at the 2.30 micron wavelength relative to the 2.35 micron wavelength. Equations (5) and (6) can be solved, and the result is the following:

$$B = A_5 R'' + A_6 \quad (7)$$

$$\frac{C}{C_0} = A_7 \left[ \frac{R-1}{R''-1} \right] \quad (8)$$

where $A_5$, $A_6$ and $A_7$ are calibration constants. That is, $B = f_4(R)$ and $(C/C_0) = f_5(R, R'')$.

Figure 3:
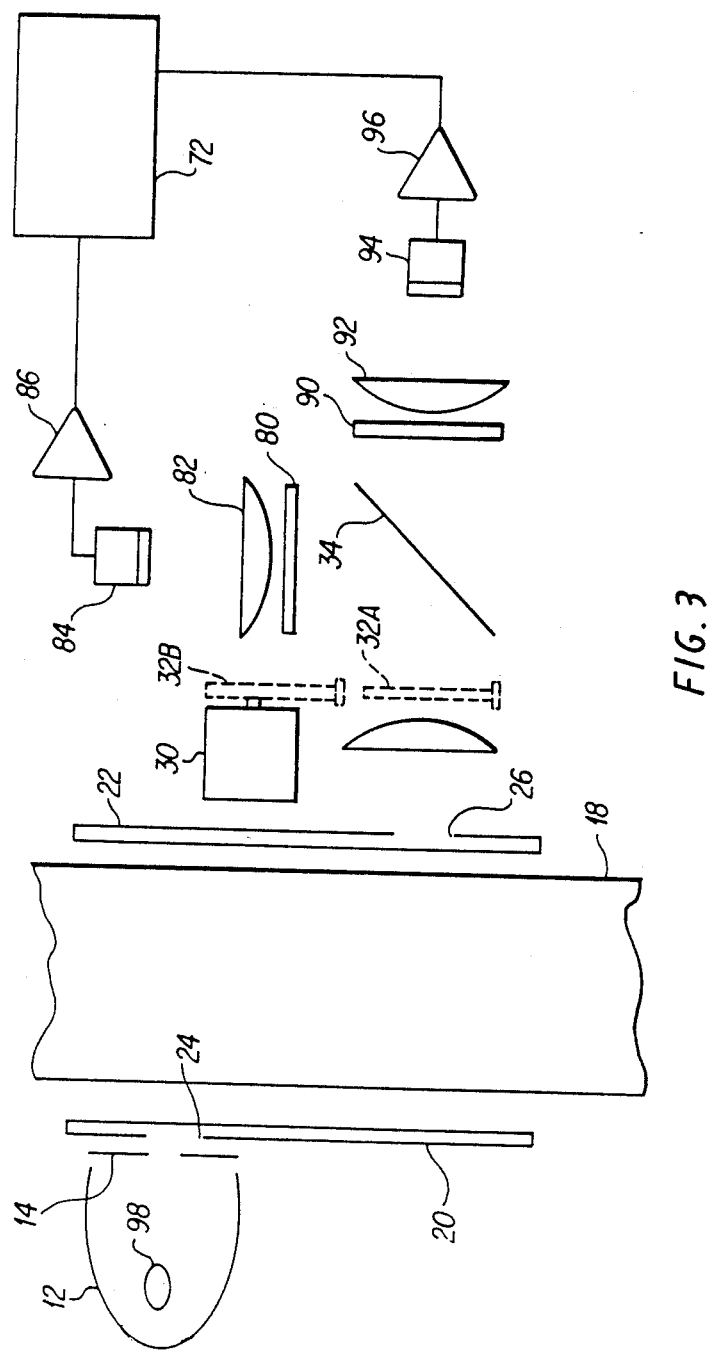
FIG. 3 is a schematic illustration of another embodiment.

Equation (7) can be used to determine the amount of binder in fiberglass and that determination is unaffected by the degree of cure. Of course, a system to utilize just equation (7) requires measurement at 2.30 and 2.35 microns, but not at 1.6 or 1.7 microns. Thus the parts of the system associated with the 1.6 and 1.7 micron measurement could be eliminated in the gauge to measure binder but not degree of cure. Such a system is shown in FIG. 3.

I have found that the embodiment shown in FIG. 2 is most effective for measurement of fiberglass having relatively low weight per unit area; whereas the embodiment shown in FIG. 1 is effective for fiberglass having relatively higher weight per unit area.

I claim:

1. A process for determining a property of fiberglass, comprising:
   (a) directing a beam of infrared radiation into the fiberglass, the beam including at least first, second, third and fourth wavelengths of radiation;
   (b) measuring the intensity of the beam at said first, second, third and fourth wavelengths after the beam has been transmitted through the fiberglass;
   (c) determining the value of a cure-sensitive function of the measured intensities of the beam at the first and second wavelengths;
   (d) determining the value of a cure-insensitive function of the measured intensities of the beam at the third and fourth wavelengths and
   (e) determining the property of the fiberglass from a combination of the values of both the cure-sensitive and cure-insensitive functions.

2. A process according to claim 1, wherein the property is the degree of cure, and wherein the degree of cure is determined using the equation:

$$\frac{C}{C_o} = A \frac{R-1}{R''-1}$$

where:
   R = the intensity of the beam at said first wavelength divided by the intensity of the beam at said second wavelength after the beam has been transmitted through the fiberglass;
   R" = the intensity of the beam at said third wavelength divided by the intensity of the beam at said fourth wavelength after the beam has been transmitted through the fiberglass;
   A is a constant;
   C = the degree of cure;
   $C_0$ = the degree of nominal cure.

3. A process according to claim 1 wherein said second wavelength is sensitive to the degree of cure and said first, third and fourth wavelengths are substantially insensitive to the degree of cure.

4. A process according to claim 1 wherein said first wavelength is about 1.6 microns, said second wavelength is about 1.7 microns, said third wavelength is about 2.30 microns and said fourth wavelength is about 2.35 microns.

5. A process according to claim 1, wherein the cure-sensitive function includes a ratio of the measured intensities of the first and second wavelengths and the cure-insensitive function includes a ratio of the measured intensities of the third and fourth wavelengths.

6. A system for determining a property of fiberglass, comprising:
   (a) source means for generating and directing a beam of infrared radiation into the fiberglass, the beam including at least first, second, third and fourth wavelengths of radiation;
   (b) detector means for measuring the intensity of the beam at said first, second, third and fourth wavelengths after the beam has been transmitted through the fiberglass; and
   (c) means for developing a cure-sensitive function of the measured intensities of the beam at the first and second wavelengths and a cure-insensitive function of the measured intensities of the beam at the third and fourth wavelengths, and for determining the property of the fiberglass from a combination of both the cure-sensitive and the cure-insensitive functions.

7. The system according to claim 6, wherein the cure-sensitive function includes a ratio of the measured intensities of the first and second wavelengths and the cure-insensitive function includes a ratio of the measured intensities of the third and fourth wavelengths.

8. A process for determining the quantity of binder in fiberglass comprising:
   (a) directing a beam of infrared radiation into the fiberglass, the beam including at least first and second wavelengths of radiation having wavelengths of about 2.30 and 2.35 microns respectively;
   (b) measuring the intensity of the beam at said first and second wavelengths after the beam has been transmitted throught the fiberglass; and
   (c) determining a cure-insensitive value indicative of the quantity of the binder in the fiberglass from the ratio of the measured intensities of said two wavelengths.

9. A process according to claim 8 wherein the quantity of binder is determined using the equation:

$$B = A_5 R'' + A_6$$

where:
   R" = the intensity of the beam at said first wavelength divided by the intensity of the beam at said second wavelength after the beam has been transmitted through the fiberglass;
   $A_5$ and $A_6$ are constants; and
   B = the amount of binder in the fiberglass.

* * * * *